US009181243B2

(12) United States Patent
Hu et al.

(10) Patent No.: US 9,181,243 B2
(45) Date of Patent: Nov. 10, 2015

(54) SOLVATE FORM M OF TRAMETINIB DIMETHYL SULFOXIDE AND METHODS OF MAKING AND USING THEREOF

(71) Applicant: HANGZHOU PUSHAI PHARMACEUTICAL TECHNOLOGY CO., LTD., Hangzhou, Zhejiang (CN)

(72) Inventors: Chenyang Hu, Hangzhou (CN); Xiaoxia Sheng, Hangzhou (CN); Xiaohong Sheng, Hangzhou (CN)

(73) Assignee: Hangzhou Pushai Pharmaceutical Technology Co. Ltd., Hangzhou (CN)

( * ) Notice: Subject to any disclaimer, the term of this patent is extended or adjusted under 35 U.S.C. 154(b) by 0 days.

(21) Appl. No.: 14/320,284

(22) Filed: Jun. 30, 2014

(65) Prior Publication Data
US 2015/0152100 A1 Jun. 4, 2015

(51) Int. Cl.
*A61K 31/519* (2006.01)
*C07D 471/04* (2006.01)
(52) U.S. Cl.
CPC ........... *C07D 471/04* (2013.01); *C07B 2200/13* (2013.01)
(58) Field of Classification Search
CPC ..................... A61K 31/519; C07D 471/04
USPC ........................ 514/264.1; 544/279
See application file for complete search history.

(56) References Cited

FOREIGN PATENT DOCUMENTS

WO    WO 2014/066606    *   5/2014

OTHER PUBLICATIONS

Jordan, V. C. Nature Reviews: Drug Discovery, 2, 2003, 205.*
Hackam, et al. JAMA, 296(14), 2006, 1731-1732.*

* cited by examiner

*Primary Examiner* — Douglas M Willis
(74) *Attorney, Agent, or Firm* — DLA Piper LLP (US)

(57) ABSTRACT

The present invention relates to a crystalline Form M of trametinib dimethyl sulfoxide solvate. Comparing with the prior art, Form M is a more stable crystalline form with better particle size distribution and good flowability and is non-hygroscopic. Therefore, it is more suitable for formulation. The present invention also relates to pharmaceutical compositions thereof, methods of making and using thereof. Trametinib dimethyl sulfoxide solvate has a structure as shown below:

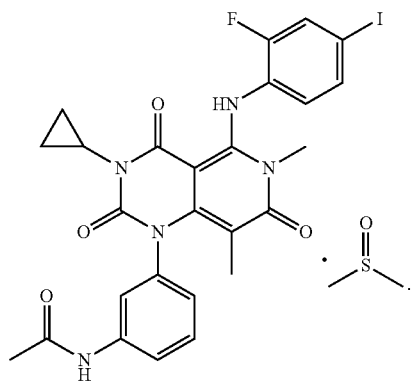

23 Claims, 6 Drawing Sheets

SOLVATE FORM M OF TRAMETINIB DIMETHYL SULFOXIDE AND METHODS OF MAKING AND USING THEREOF

RELATED APPLICATION

This application claims priority to Chinese Patent Application 201310697357.5, entitled "Solvate form M of Trametinib Dimethyl Sulfoxide and Methods of Making and Using Thereof" filed on Dec. 3, 2013, which is hereby incorporated by reference herein in its entirety.

FIELD OF THE INVENTION

This invention relates to the field of crystallization technology in pharmaceutical chemistry; more specifically, the present invention relates to a crystalline form M of trametinib dimethyl sulfoxide solvate, pharmaceutical compositions thereof, and methods of preparation and use thereof.

BACKGROUND OF THE INVENTION

Trametinib, also known as GSK1120212, GSK212 or JTP74057, is conventionally named: N-{3-[3-cyclopropyl-5-(2-fluoro-4-iodo-phenylamino)-3,4,6,7-tetrahydro-6,8-dimethyl-2,4,7-trioxo-pyrido[4,3-d]pyrimidin-1(2H)-yl]phenyl}acetamide. The formula of this compound is as the following:

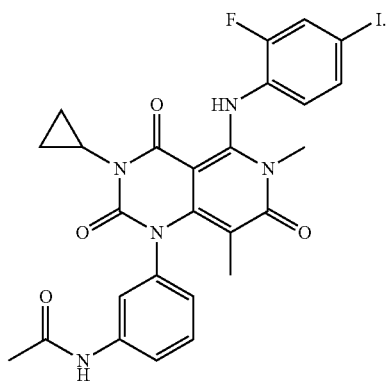 [SMILES: CC(=O)Nc1cccc(-n2c(=O)n(C3CC3)c(=O)c3c(Nc4ccc(I)cc4F)n(C)c(=O)c(C)c32)c1]

Trametinib, developed by GlaxoSmithKline (GSK), is a new targeted drug for the treatment of melanoma. It is a powerful and selective MEK1/MEK2 inhibitor which can effectively prevent cancer cell proliferating and can induce cell apoptosis, and increase the life of patients. Phase III clinical trials show that the therapeutic effect of trametinib is significantly better than traditional chemotherapy drugs for treatment of advanced melanoma with BRAF V600E/K mutations and for treatment of BRAF V600E or V600K mutation-positive metastatic cutaneous melanoma. In addition, studies on therapeutic effect of Trametinib in combination with other cancer drugs is on the way and show very encouraging results. The dosage form of Trametinib include oral coating tablets, in which trametinib dimethyl sulfoxide solvate is the active ingredient (also known as GSK 1120212B). Each tablet contains 0.5 mg, 1 mg or 2 mg of Trametinib. The standard target content of dimethyl sulfoxide in Trametinib tablets is approximately 11.3 wt %(theoretical value), and the lower dimethyl sulfoxide content is approximately 9.5 wt %. Trametinib is also available in oral liquid dosage form.

Trametinib and its preparation methods were described in patent document WO2005121142A1 which discloses its $^1$H-NMR data. Also, WO2005121142A1 published trametinib dimethyl sulfoxide solvate. Although an example in WO2005121142A1 describes that trametinib dimethyl sulfoxide solvate can be obtained by conventional methods, neither detailed methods of the preparation, nor the stoichiometry of the trametinib dimethyl sulfoxide solvate, nor its characterization data were given except the $^1$H-NMR data.

The present inventors have found that trametinib dimethyl sulfoxide solvate can be obtained using the conventional methods in the field. However, the trametinib dimethyl sulfoxide solvate obtained by the conventional methods is not stable and is easy to transform its crystalline form. For example, the XRPD of the trametinib dimethyl sulfoxide solvate obtained by the conventional methods, when stored at a degree of 44% RH (relative humidity) under room temperature for a period of time (e.g., 9 months), its patterns changed, showing a form change in the solvate.

Therefore, in order to meet the strict requirements for crystalline forms of active ingredients in different pharmaceutical dosage forms, there is a need for the development of a more stable trametinib dimethyl sulfoxide solvate.

SUMMARY OF THE INVENTION

In one aspect, the present invention provides a crystalline form of trametinib dimethyl sulfoxide solvate Form M, pharmaceutical compositions thereof, and methods of making and using thereof.

The crystalline form M of trametinib dimethyl sulfoxide solvate (hereinafter named "Form M" for convenience), is a solvated form of trametinib at 1:1 molar ratio of trametinib to dimethyl sulfoxide, and has a formula as the following:

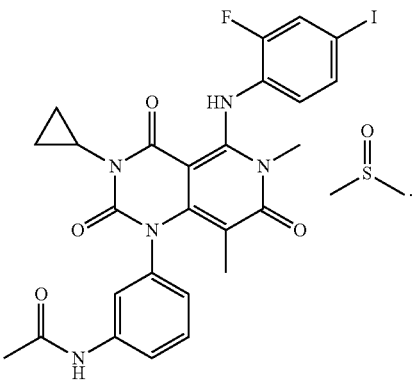

According to the present invention, Form M is characterized by a powder X-ray diffraction pattern measured using Cu-Kα radiation comprising the following specific peaks at 2θ values: 7.8±0.2°, 11.4±0.2°, 16.8±0.2°, 18.6±0.2°, 20.0±0.2°, 23.3±0.2° and 26.5±0.2°.

In a further aspect, Form M is characterized by a powder X-ray diffraction pattern measured using Cu-Kα radiation comprising the following specific peaks at 2θ values: 7.8±0.2°, 11.4±0.2°, 16.8±0.2°, 18.4±0.2°, 18.6±0.2°, 20.0±0.2°, 20.3±0.2°, 23.3±0.2°, 26.5±0.2° and 27.9±0.2°.

In a further aspect, Form M is characterized by a powder X-ray diffraction pattern measured using Cu-Kα radiation comprising the following specific peaks at about 2θ values and relative intensity:

| Angle 2θ | Relative Intensity % |
| --- | --- |
| 7.8 ± 0.2° | 17.0 |
| 11.4 ± 0.2° | 100.0 |
| 16.8 ± 0.2° | 16.3 |
| 18.4 ± 0.2° | 10.5 |
| 18.6 ± 0.2° | 15.3 |
| 20.0 ± 0.2° | 49.0 |
| 20.3 ± 0.2° | 22.1 |
| 20.9 ± 0.2° | 14.3 |
| 21.1 ± 0.2° | 21.7 |
| 23.3 ± 0.2° | 47.9 |
| 25.4 ± 0.2° | 20.4 |
| 26.5 ± 0.2° | 32.9 |
| 27.9 ± 0.2° | 16.5 |
| 28.3 ± 0.2° | 19.3 |

Non-limitingly, the Form M has a typical powder X-ray diffraction (XRPD) pattern as shown in FIG. 3.

The Fourier transform infrared spectrum of the Form M comprises the following characteristic peaks expressed by wavenumbers at about: 791, 1034, 1280, 1304, 1319, 1418, 1489, 1544, 1589, 1635 and 3079 $cm^{-1}$.

The Thermogravimetric Analysis (TGA) plot of the Form M shows it has 11.1% weight loss before 250° C., equaling containing about one molecule of dimethyl sulfoxide.

The Differential Scanning calorimetry (DSC) diagram of the Form M shows it has an endothermic peak between 160-190° C., with a melting point of 170.3° C.

The isothermal sorption curve of the Form M shows it has about 1.07% of weight change between 20-80% RH (relative humidity), indicating it is non-hygroscopic.

The methods for preparing the Form M characterized in that, comprises any of the following preparing methods (1)-(3), described below.

(1) suspending trametinib in dimethyl sulfoxide, stirring at room temperature for 3 to 10 days to crystallize and recovering the Form M.

Preferably, the ratio of trametinib and dimethyl sulfoxide is 30 to 50 mg:1 mL, more preferably, is 40 to 50 mg:1 mL.

Preferably, the duration of crystallization is 3 to 7 days.

(2) Suspending other trametinib dimethyl sulfoxide solvates than Form M in dimethyl sulfoxide and stirring at room temperature for 3 to 10 days to crystallize, recovering the Form M.

Preferably, the ratio of another trametinib dimethyl sulfoxide solvate form other than Form M and dimethyl sulfoxide is 30 to 50 mg:1 mL, more preferably, is 40 to 50 mg:1 mL.

Preferably, the duration of crystallization is 3 to 7 days.

(3) Cooling the solution of trametinib in dimethyl sulfoxide from 50° C. to 20° C. with a cooling rate of 2 to 10° C./hour, stirring at 20° C. for 10 to 24 hours to crystallize and recovering the Form M.

Preferably, the concentration of the solution of trametinib in dimethyl sulfoxide is 30 to 60 mg/mL, more preferably, is 50 to 60 mg/mL.

Preferably, the solution is cooled from 40° C. to 20° C.

Preferably, the cooling rate is 2 to 5° C./hours.

Preferably, the duration of the stirring is 10 to 16 hours.

The Form M obtained from the above said preparation methods can be further isolated and dried. The "Isolated" can use common isolation methods in this field, such as filtration and centrifuge. The "filtration" generally is done at room temperature with a pressure less than normal atmosphere, preferably, at a pressure less than 0.09 MPa. The detailed operation of centrifuge in a lab comprises: put the suspended sample in a centrifuge tube, centrifuge at 6000 rotation/min until all solids are at the bottom of the tube. The "drying" can be done using common technology in this field, such as drying at room temperature in a hood, drying with air blowing in a conventional oven, or drying at reduced pressure in a vacuum oven; can choose either at normal pressure or at reduced pressure, preferably at a pressure less than 0.09 MPa. The drying temperature is 20-40° C., drying time is 10-72 hours, preferably is 10 to 48 hours, more preferably is 10-24 hours.

In the above preparation methods: the term "room temperature" can be 10 to 30° C.; the term "stirring" refers to common stirring methods in this field, such as stirring under magnetic forces or mechanical stirring, the speed of stirring is 50-1800 rotation/min, preferably is 300-900 rotation/min.

It should be mentioned specifically that, the Polarized Light Microscopy (PLM) plot and the Particle Size Distribution (PSD) plot of the Form M obtained by the above preparing method (1) or (2) show fine and uniformly-distributed particles, and the PSD plot of the Form M obtained by the above preparing method (3) show larger and uniformly distributed particles.

In some embodiments, when the trametinib dimethyl sulfoxide solvate Form M is produced by the preparing method (3), typical particle size distribution (PSD) of the Form M in volume based shows $D_{50}$ of the particles may be at least about 10 μm, such as about 10-50 μm, and/or $D_{10}$ may be at least about 5 μm, such as about 5-20 μm, and/or $D_{90}$ of at least about 30 μm, such as about 30-100 μm.

The present invention overcomes the drawbacks of the prior art by providing trametinib dimethyl sulfoxide solvate Form M. The Form M shows useful properties and applications as the following:

(1) The Form M is a stable crystalline form. When stored at 44% RH under room temperature for 9 months, its XRPD patterns show no signs of form change, as contrary to other trametinib dimethyl sulfoxide solvate(s), such as trametinib dimethyl sulfoxide solvates obtained by conventional methods, which changed its XRD pattern when stored at the same condition. Therefore, the Form M is more suitable for pharmaceutical applications as it less likely to undergo form change during production and storage.

(2) Other trametinib dimethyl sulfoxide solvates (for example, trametinib dimethyl sulfoxide solvates obtained by conventional methods), if stirred in dimethyl sulfoxide at room temperature, transform to Form M, demonstrating that Form M is more stable than other trametinib dimethyl sulfoxide solvates at room temperature.

(3) The Form M is non-hygroscopic, providing better processability for preparing formulations than the known trametinib dimethyl sulfoxide solvates, also it can adapt to various humidity conditions during storage and transportation.

(4) Trametinib dimethyl sulfoxide solvates obtained by conventional methods are very fine particles, making filtering and processing difficult. However, in the present invention, special processes described herein produced trametinib dimethyl sulfoxide solvate Form M with larger and uniformly-distributed particles, which may promote good flowability, reduce filtering time and make tableting or capsulating process easier.

(5) The raw material trametinib contains at least about 0.4% by weight of an impurity (hereinafter "A impurity"), its formula as the following.

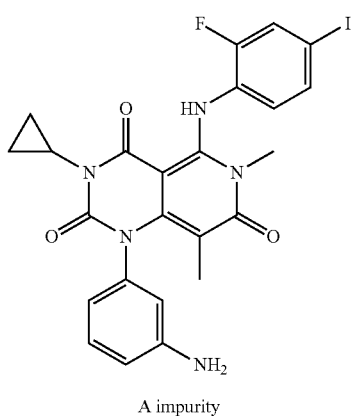 [SMILES: Cc1c(=O)n(C)c(Nc2ccc(I)cc2F)c2c(=O)n(C3CC3)c(=O)n(-c3cccc(N)c3)c12]

A impurity

Using trametinib as the raw material, trametinib dimethyl sulfoxide solvates produced by conventional methods contain about 0.25% by weight of A impurity. When using trametinib as the raw material, trametinib dimethyl sulfoxide solvate Form M produced by the present invention contains less than 0.15% by weight of A impurity; in some embodiments, for example the Form M produced by the preparing method (3), contains less than 0.10% by weight of A impurity. Having an active ingredient with lower impurity content is advantageous to pharmaceutical compositions, it lowers the risks of instability, as the latter may cause therapeutic efficacy and safety problem. In the present invention, impurities were identified using HPLC method.

The trametinib dimethyl sulfoxide solvate Form M in present invention is a pure, single component, essentially not containing any other crystalline forms. In the present application, "essentially not containing" means this form has less than 20 wt % of any other forms, particularly less than 10 wt % of any other forms, more particularly less than 5 wt % of any other forms, even more particularly less than 1 wt % of any other forms.

In the present invention, the term "form" means it has been confirmed by X-ray diffraction pattern. It can be understood by a skilled person in this field that its experimental errors depend on the instrumentation, the sample preparation and sample purity. Especially, the X-ray diffraction pattern usually can change with various instrument conditions. In particular, the relative intensity of the diffraction peak can change with the change of the experiment conditions, so the relative intensity of the diffraction peaks can not be used as a sole or determinative factor in crystalline form assignment. In addition, the experimental error of 2-theta angle usually is within 5% or even less, the angle error should also be taken into consideration, usually within ±0.2° is acceptable. In addition, influenced by sample preparations such as sample height or other experimental conditions, overall shift of diffraction peak sometime occurs and should be taken into consideration. Therefore, it could be understood by a skilled person in this field that any forms with the same or similar characteristic peaks are considered belonging to the present invention.

The starting material trametinib in the present invention can be prepared referring to the preparation method in the step 8 of example 4-1 in Patent document WO2005121142A1, its content is incorporated herein by reference.

In a further aspect, the present application provides a pharmaceutical composition, the pharmaceutical composition includes a therapeutically and/or preventively effective amount of trametinib dimethyl sulfoxide solvate Form M in the present invention or prepared according to the present invention, and at least one pharmaceutically acceptable excipient(s). In addition, the pharmaceutical composition may also include other pharmaceutical crystalline forms or amorphous forms or salts of trametinib. Optionally, the pharmaceutical composition may also include one or more other pharmaceutical active ingredients such as other compounds having antitumor activity.

The pharmaceutically acceptable excipient(s) in the pharmaceutical compositions include but not limit to: binder, such as: acacia gum, guar gum, gelatine, vinylpolypyrrolidone, hydroxypropyl cellulose, hydroxypropyl methylcellulose, hydroxyethyl cellulose, polyethylene glycol, copovidone, etc; diluents, such as starch, modified starch, lactose, powered cellulose, microcrystalline cellulose, calcium dihydrogenphosphate, tricalcium phosphate, mannitol, sorbitol and sugar, etc; disintegrators, such as starch, carboxymethyl starch sodium, sodium starch glycollate, pregelatinized starch, cross-liked polyvinyl pyrrolidone, croscarmellose sodium and colloidal silicon dioxide, etc; lubricants, such as stearic acid, magnesium stearate, zinc stearate, sodium benzoate and sodium acetate, etc; glidants, include but are not limited to colloidal silicon dioxide; complex formation former, such as various grades of cyclodextrin and resin; release modifier, such as hydroxypropyl cellulose, carboxy methyl cellulose, hydroxypropyl methyl cellulose, ethyl cellulose, methyl cellulose, methyl methacrylate and wax, etc.

Other pharmaceutically acceptable excipients include, but not limit to: film forming agent, plasticizer, coloring agent, flavorings, viscosity modifiers, preservatives, stabilizers, buffers and antioxidants, etc.

The pharmaceutical compositions could be tablets (include uncoated tablets, film-coated tablets, sugar coated tablets, enteric-coated tablets, etc), pills, powders, granules, capsules, syrups, emulsions, suspensions, injections, solutions, suppository, tinctures, elixirs, aerosols, ophthalmic preparations and lyophilized preparations, etc. The routes of administration could be systematical or local, oral or non-oral. A preferred route of administration usually is an oral route that gives good bioavailability and can keep long term blood/plasma concentration of drug(s).

The pharmaceutical compositions can be prepared in accordance with ordinary skills and conventional means in the art. When preparing the pharmaceutical compositions, trametinib dimethyl sulfoxide solvate Form M in the present invention could be mixed with one or more pharmaceutically acceptable excipients, optionally with one or more other pharmaceutically active ingredients. Solid dosage forms can be prepared by direct mixing, granulation and other methods.

Furthermore, the present invention describes the use of trametinib dimethyl sulfoxide solvate Form M in the manufacture of a medicament for treatment and/or preventing hyperproliferative disorders, which includes, for example, tumors, specifically brain tumor (malignant astroglioma and gliomas such as oligodendroglioma), esophageal cancer, gastric cancer, liver cancer, pancreatic cancer, colorectal cancer, lung cancer (non-small cell lung cancer, small cell lung cancer, primary or metastic squamous cell carcinoma, etc), kidney cancer, breast cancer, ovarian cancer, prostate cancer, skin cancer, melanoma, neuroblastoma, sarcoma, osteochondroma, osteoma, osteosarcoma, seminoma, extragonadal germ cell tumors, testicular tumor, uterus tumor (cervical cancer, endometrial carcinoma), head and neck tumor (maxilla cancer, throat cancer, nasopharyngeal carcinoma, tongue cancer, intraoral cancer, etc), multiple myeloma, malignant lymphoma (reticulum cell sarcoma, lymphosarcoma, Hodgkin's disease), polycythemia vera, leukemia (acute myeloid leukemia, chronic myeloid leukemia, acute lymphoblastic leukemia, chronic lymphoblastic leukemia), thyroid tumor, renal pelvic cancer, ureter tumor, bladder tumor, gallbladder cancer, cholangiocarcinoma, choriocarcinoma, melanoma and pediatric tumors (Ewing's sarcoma, Wilm's tumor, rhabdomyosarcoma, hemangiosarcoma, testis embryonal cancer, neuroblastomas, retinoblastoma, hepatoblastoma), etc. preferably applied in treatment of brain tumor (malignant astroglioma and gliomas such as oligodendroglioma), esophageal cancer, gastric cancer, liver cancer, pancreatic cancer, colorectal cancer, lung cancer (non-small cell lung cancer, small cell lung cancer, primary or metastic squamous cell carcinoma, etc), kidney cancer, breast cancer, ovarian cancer, prostate cancer, skin cancer, melanoma, neuroblastoma, sarcoma; more preferably applied in treatment of colorectal cancer, pancreatic cancer, kidney cancer, lung cancer, breast cancer and melanoma.

In addition, the trametinib dimethyl sulfoxide solvate Form M in the present invention could relate to the treatment of chronic pains, in specific, neuralgia, acute pain, pains relate to chronic alcoholic intoxication, avitaminosis, uremia and hypothyroidism. In addition, could relate to diseases related to neutrophil, in specific, ischemia-reperfusion injury, chronic obstructive pulmonary disease, acute respiratory syndrome, cysticfibrosis, idiopathic, pulmonary fibrosis, sepsis, endotoxemia, pulmonary emphysema, and asbestosis. In addition, could relate to transplant rejection. In addition, could relate to arthritis, in specific rheumatoid arthritis and osteoarthritis. In addition, could relate to asthma. In addition, could relate to viral disease, specifically herpes simplex virus HSV-1 infection, human cytomegalovirus (HCMV) infection and human Immunodeficiency Virus (HIV) infection. In addition, could relate to diseases caused by cartilage degeneration or damage, specifically osteoarthritis, rheumatoid arthritis, osteochondritis dissecans and diseases that require cartilage formation.

Furthermore, the present invention provides a method for treatment and/or preventing hyperproliferative disorders. The method includes providing patients in need trametinib dimethyl sulfoxide solvate Form M in the present invention or pharmaceutical compositions comprising trametinib dimethyl sulfoxide solvate Form M described in present invention. The hyperproliferative disorders, preferably brain tumor, esophageal cancer, gastric cancer, liver cancer, pancreatic cancer, colorectal cancer, lung cancer, kidney cancer, breast cancer, ovarian cancer, prostate cancer, skin cancer, melanoma, neuroblastoma and sarcoma; more preferably applied in treatment of colorectal cancer, pancreatic cancer, kidney cancer, lung cancer, breast cancer and melanoma; the patients refer to mammals including human beings. The dosage for adults is 0.01 mg to 1 gram which is administered once or several times a day in oral or parental dosage forms.

DETAILED DESCRIPTION OF EMBODIMENTS THE INVENTION

Figure 1:
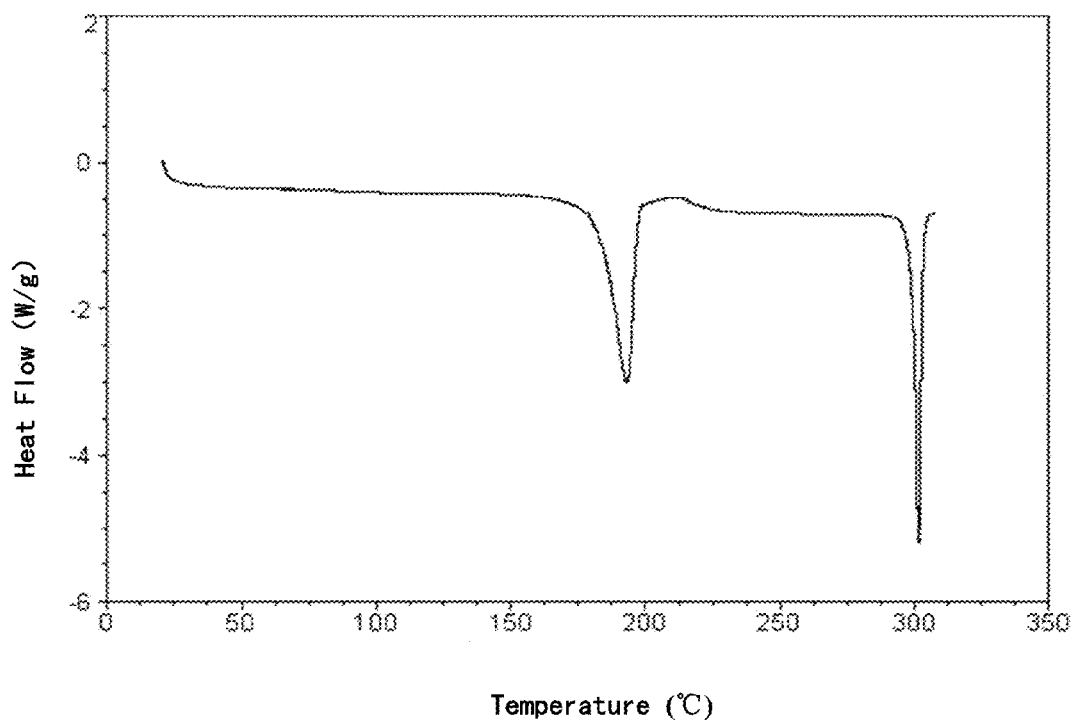
FIG. 1. The DSC thermogram of trametinib dimethyl sulfoxide solvate prepared by conventional method described in Reference Example 1.

The invention is illustrated herein by means of non-limiting Examples, which described the solvate Form M and its preparation and application in details. It will be apparent to the skilled person in this field that various changes in materials and methods in the embodiments described may occur without deviating from the scope or spirit of this invention.

Instruments and Methods

X-Ray Powder Diffraction (XRPD): X-ray powder diffraction patterns were recorded using Bruker D8 Advance diffractometer equipped with θ-2θ goniometer, Mo monochromator and Lynxeye detector. Data were collected by Diffrac Plus XRPD Commander software. The instrument was calibrated by known standards such as corundum before use. Typical procedures: Place the specimen on a zero background plate, scan at room temperature using Cu-Ka X-radiation ($\lambda=1.5406$ Å) at 40 kV and 40 mA. Diffraction patterns were collected over 2θ range of 3-40° with a step size of 0.02° and a speed of 0.2 second/step.

Polarized Light Microscope (PLM): Specimens were examined using an XP-500E polarized light microscope (Shanghai Changfang Optical Instruments, LLC). Typical procedure: Place some specimen on a glass plate, add some mineral oil to disperse the specimen, place a cover slip, place the specimen on the loading table, exam the specimen under the microscope using appropriate magnitudes and take pictures if necessary.

Typical particle size distribution (PSD) is measured using a laser diffraction particle size analyzer, namely Microtrac FLEX 53500. The most common approach for defining the distribution is to report the $D_{10}$, $D_{50}$, and $D_{90}$ values based on a volume distribution. The $D_{50}$, the median, has been defined above as the diameter where half of the population lies below this value. Similarly, 90 percent of the distribution lies below the $D_{90}$, and 10 percent of the population lies below the $D_{10}$.

Differential Scanning calorimeter (DSC): DSC was performed by TA Instruments Q200 MDSC. The control software is Thermal Advantage. Typically about 1-10 mg of the specimen was placed in an aluminum DSC pan and heated from room temperature to 310° C. at 10° C./min under dry nitrogen purge (at a flow rate of 40 mL/min), the heat changes of the specimen during the course were recorded by the TA software simultaneously. In the present invention, the melting points are reported using DSC onset temperature.

Thermogravimetric analysis (TGA): TGA was performed by TA Instruments Q500 TGA. The control software is Thermal Advantage and the analysis software is Universal Analysis. Usually 5-15 mg of the specimen was placed in the platinum pan and heated from room temperature to 400° C. at 10° C./min under dry nitrogen purge (at a flow rate of 40 mL/min), the heat changes of the specimen during the course were recorded by the TA software simultaneously. The segment measure mode with high resolution was used.

Isothermal sorption was performed by TA Instruments Q5000 TGA. The control software is Thermal Advantage and the analysis software is Universal Analysis. Usually 1 to 10 mg of the specimen was placed in the platinum pan. The weight changes of the sample from 20% to 80% to 20% relative humidity were recorded by the TA software and the isothermal sorption plot was obtained by the analysis software.

Fourier Transform Infrared Spectroscopy (FTIR): FTIR spectra were collected by Bruker Tensor 27 with software OPUS. Usually Attenuated Total Reflection (ATR) mode was used. The samples were scanned between 4000 $cm^{-1}$ and 600 $cm^{-1}$. Scanning time of the samples or the blank background: 16 seconds, resolution: 4 $cm^{-1}$.

HPLC Chromatographic conditions:

Equipment: Agilent 1100 HPLC system equipped with a UV detector.

Column: Welch Xtimate C18, 5 μm, 150×4.6 mm. Column temperature: Ambient.

Flow rate: 1.0 mL/min.

wavelength: 254 nm injection volume: 5 μl diluent: mobile phase A: mobile phase B=1:1 mobile phase A: water (contains 0.05% TFA) mobile phase B: Acetonitrile elution mode: gradient

| Time(minutes) | % mobile phase A | % mobile phase B |
|---|---|---|
| 0 | 90 | 10 |
| 15 | 20 | 80 |
| 20 | 20 | 80 |
| 20.01 | 90 | 10 |
| 25 | 90 | 10 |

Reagents referred in the present invention are commercially available unless otherwise stated.

In the present invention, experiments were carried out at room temperature unless otherwise stated.

In the present invention, the ultrasonic treatment to facilitate dissolution was conducted by placing suspensions (in containers) in an ultrasonic cleaner, typically treated at 40 KHz.

EXAMPLES

Reference Example 1

Trametinib dimethyl sulfoxide solvate was obtained by a conventional method such as cooling recrystallization.

A solution of trametinib (500.0 mg) in dimethyl sulfoxide (2.5 mL) was heated from room temperature to 80° C. with stirring to dissolve. The solution was further stirred for 2 hours and then precipitation was observed. The suspension was stirred at 80° C. for another 3 hours and cooled to room temperature and then stirred over night. The precipitate was collected by filtration and dried under reduced pressure at 30° C. for 16 hours to give trametinib dimethyl sulfoxide solvate.

The X-Ray powder diffraction pattern of trametinib dimethyl sulfoxide solvate obtained by the above conventional method shows the following specific peaks at about 2θ values and relative intensity:

| Angle 2θ | Relative Intensity % |
|---|---|
| 7.5 ± 0.2° | 27.5 |
| 8.2 ± 0.2° | 19.2 |
| 11.1 ± 0.2° | 100.0 |
| 13.7 ± 0.2° | 18.5 |
| 15.5 ± 0.2° | 23.3 |
| 18.1 ± 0.2° | 48.2 |
| 19.2 ± 0.2° | 25.2 |
| 19.6 ± 0.2° | 64.6 |
| 20.4 ± 0.2° | 27.1 |
| 20.7 ± 0.2° | 64.1 |
| 22.8 ± 0.2° | 72.9 |
| 24.8 ± 0.2° | 26.2 |
| 26.0 ± 0.2° | 33.7 |
| 27.3 ± 0.2° | 27.0 |
| 27.7 ± 0.2° | 23.8. |

Its DSC thermogram is shown in FIG. 1. FIG. 1 indicates an endothermic peak is between 160-190° C. with a melting point of 183.8° C.

Figure 2:
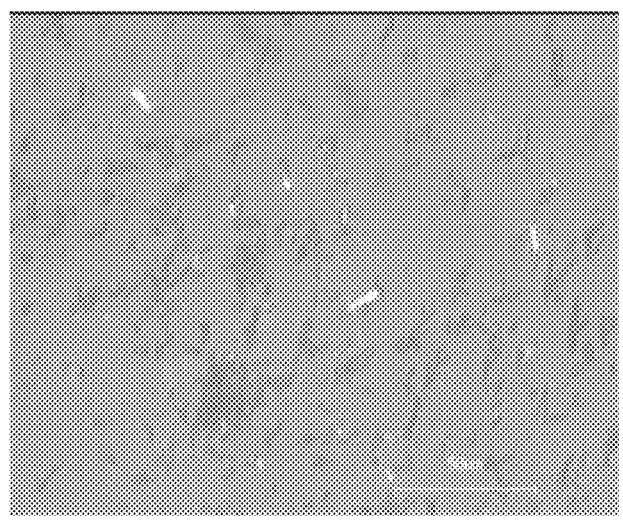
FIG. 2. PLM plot of trametinib dimethyl sulfoxide solvate prepared by conventional method described in Reference Example 1.

Its PLM plot is shown in FIG. 2. FIG. 2 indicates very fine crystals.

Its HPLC content of A impurity is 0.25 wt %.

Reference Example 2

Trametinib dimethyl sulfoxide solvate was obtained by a conventional method such as distilling recrystallization.

A solution of trametinib (200.0 mg) in dimethyl sulfoxide (50.0 mL) was heated from room temperature to 80° C. The solution was concentrated under reduced pressure at 80° C. until the solvent dried up to give trametinib dimethyl sulfoxide solvate.

The product of Reference Example 2 shows same or similar X-Ray powder diffraction pattern, i.e. characteristic peaks and strength and DSC thermogram (neither listed herein) as those of Reference Example 1. These illustrate products of Reference Example 2 and Reference Example 1 are the same crystalline form.

Example 1

Under a nitrogen atmosphere, tetrahydrofuran (40 mL) was added to N-{3-[3-cyclopropyl-1-(2-fluoro-4-iodo-phenyl)-6,8-dimethyl-2,4,7-trioxo-1,2,3,4,7,8-hexahydro-pyrido[2,3-d]pyrimidin-5-ylamino]-phenyl}-acetamide (5 g) and a methanol solution (1.57 g) containing 28% sodium methoxide was added and the mixture was stirred at room temperature for 4 hours. Acetic acid (0.56 mL) was added to the mixture and the mixture was stirred at room temperature for 30 min. And then water (40 mL) was added and the mixture was further stirred for 1 hour. The crystals were collected by filtration and dried under reduced pressure at 40° C. to give trametinib (4.75 g). Its HPLC content of A impurity is 0.42 wt %.

Example 2

Dimethyl sulfoxide (2 mL) was added to trametinib (100 mg) and the mixture was treated by ultrasound at 40 KHz for 5 minutes. The mixture suspension was stirred at room temperature for 3 days to crystallize and then centrifuged. The precipitate was collected and dried under reduced pressure at 40° C. for 16 hours to give trametinib dimethyl sulfoxide solvate Form M (94.3 mg, yield 83.7%).

Figure 3:
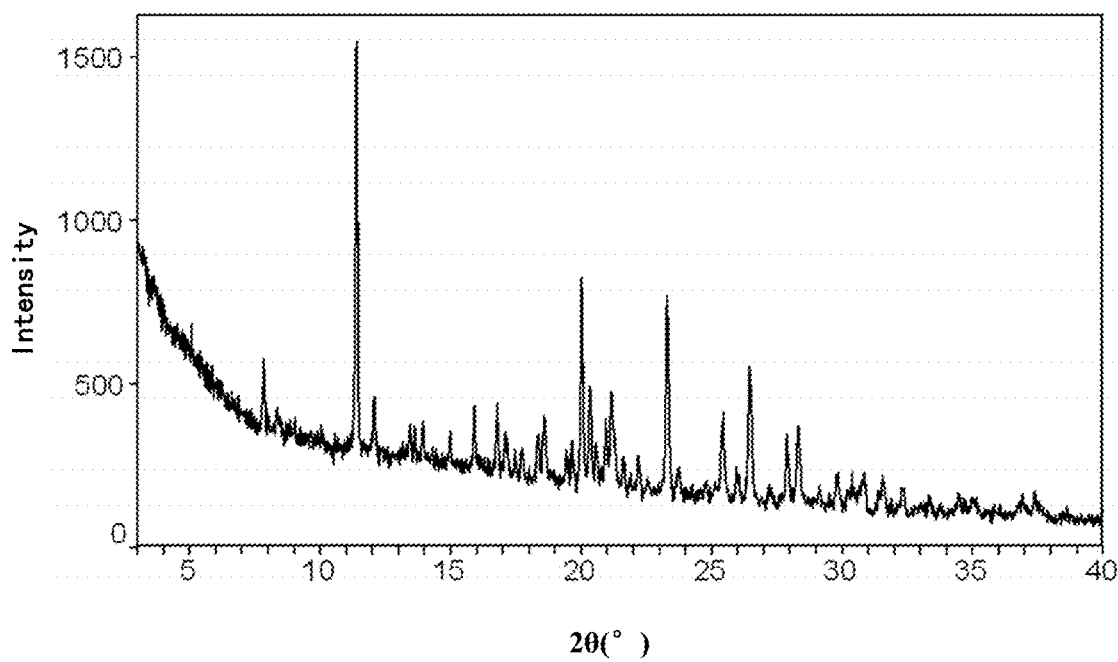
FIG. 3. XRPD pattern of trametinib dimethyl sulfoxide solvate Form M in present invention.

Its XRPD pattern is shown in FIG. 3.

Figure 4:
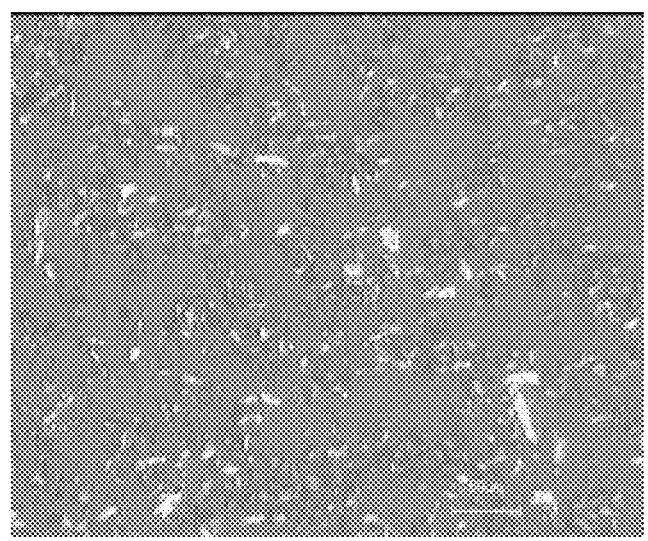
FIG. 4. PLM plot of trametinib dimethyl sulfoxide solvate Form M in Example 3.

Its PLM plot is shown in FIG. 4. FIG. 4 indicates fine crystals.

Figure 5:
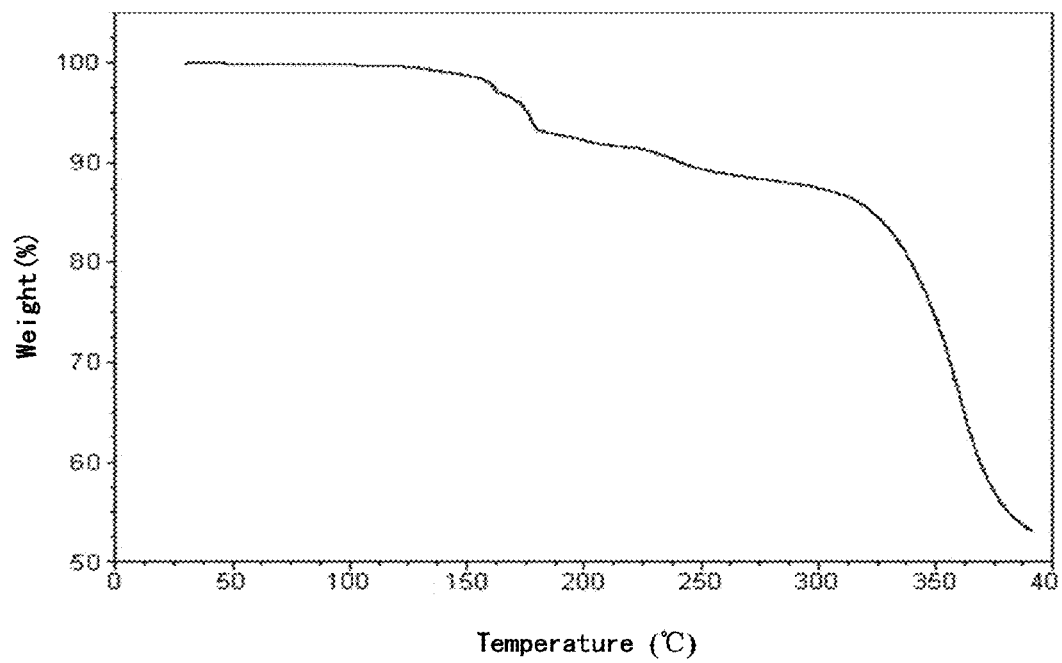
FIG. 5. TGA plot of trametinib dimethyl sulfoxide solvate Form M in present invention.

Its TGA plot is shown in FIG. 5. FIG. 5 indicates 11.1% weight loss is before 250° C., which is equal to containing about one dimethyl sulfoxide molecule.

Figure 6:
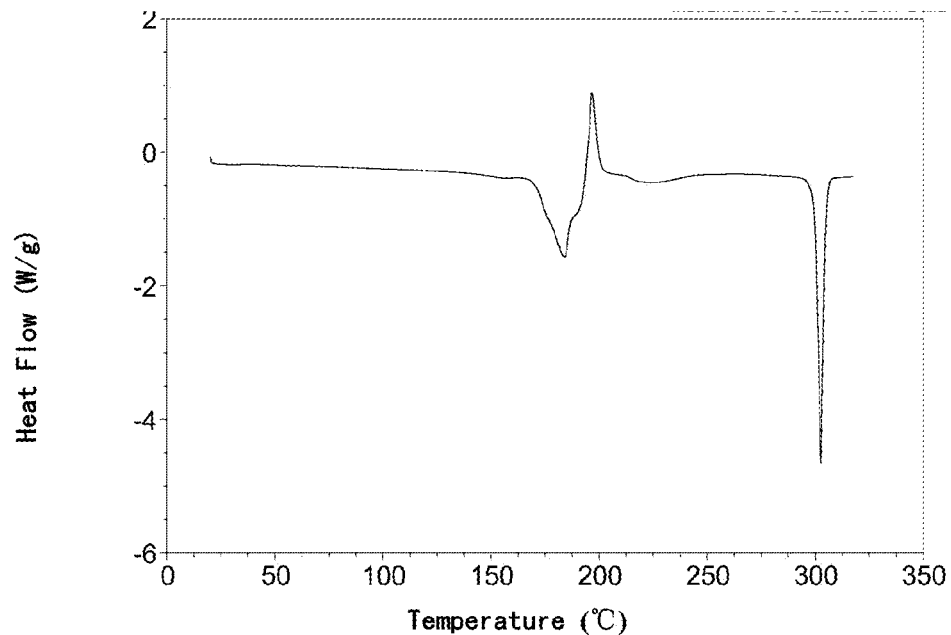
FIG. 6. DSC thermogram of trametinib dimethyl sulfoxide solvate Form M in present invention.

Its DSC thermogram is shown in FIG. 6. FIG. 6 indicates an endothermic peak is between 160-190° C. with a melting point of 170.3° C.

Figure 7:
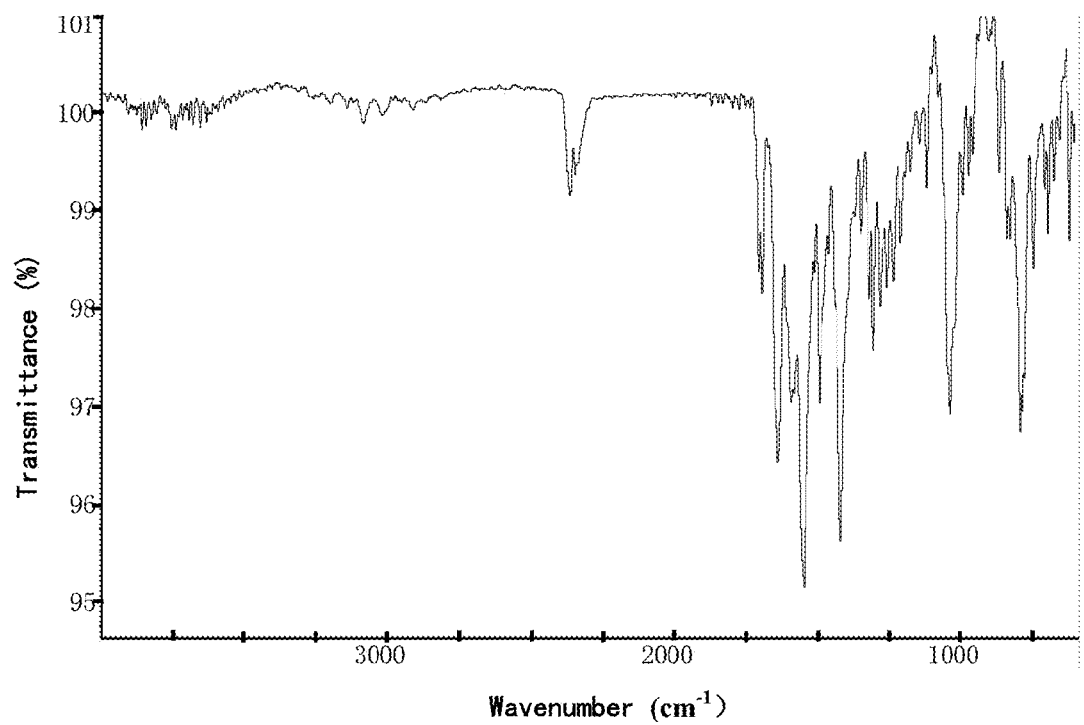
FIG. 7. IR spectrum of trametinib dimethyl sulfoxide solvate Form M in present invention.

Its IR spectrum is shown in FIG. 7.

Figure 8:
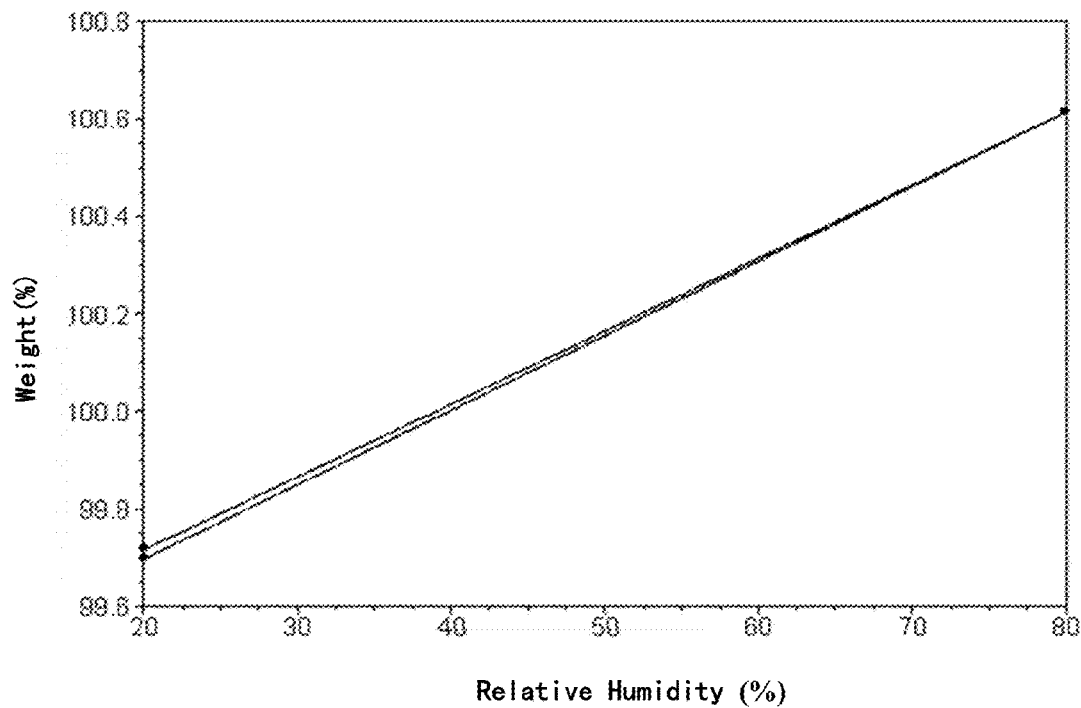
FIG. 8. Isothermal sorption plot of trametinib dimethyl sulfoxide solvate Form M in present invention.

Its isothermal sorption plot is shown in FIG. 8. FIG. 8 shows about 1.07% of weight loss between 20% and 80% relative humidity.

Its HPLC content of A impurity is 0.13 wt %.

The above results indicate that trametinib dimethyl sulfoxide solvate Form M is very stable at room temperature and is not hygroscopic.

Example 3

Dimethyl sulfoxide (2 mL) was added to trametinib (80 mg) solids and the mixture was treated by ultrasound at 40 KHz for 5 minutes. The mixture suspension was stirred at room temperature for 7 days to crystallize and then centrifuged. The precipitate was collected and dried under reduced pressure at 40° C. for 16 hours to give trametinib dimethyl sulfoxide solvate Form M (75.8 mg, yield 84.1%).

Example 4

Dimethyl sulfoxide (3 mL) was added to trametinib (90 mg) and the mixture was treated by ultrasound at 40 KHz for 5 minutes. The mixture suspension was stirred at room temperature for 10 days to crystallize and then centrifuged. The precipitate was collected and dried under reduced pressure at 40° C. for 16 hours to give trametinib dimethyl sulfoxide solvate Form M (78.3 mg, yield 77.2%).

Example 5

Dimethyl sulfoxide (2 mL) was added to trametinib dimethyl sulfoxide solvate (80 mg) made in Reference Example 1 and the mixture was treated by ultrasound at 40 KHz for 5 minutes. The mixture suspension was stirred at room temperature for 7 days to crystallize and then centrifuged. The precipitate was collected and dried under reduced pressure at 40° C. for 20 hours to give trametinib dimethyl sulfoxide solvate Form M (72.5 mg, yield 90.6%).

Its HPLC content of A impurity is 0.14 wt %.

Example 6

Dimethyl sulfoxide (3 mL) was added to trametinib dimethyl sulfoxide solvate (90 mg) made in Reference Example 2 and the mixture was treated by ultrasound at 40 KHz for 5 minutes. The mixture suspension was stirred at room temperature for 10 days to crystallize and then centrifuged. The precipitate was collected and dried under reduced pressure at 40° C. for 24 hours to give trametinib dimethyl sulfoxide solvate Form M (65.3 mg, yield 72.6%).

Example 7

Dimethyl sulfoxide (2 mL) was added to trametinib dimethyl sulfoxide solvate (100 mg) made in Reference Example 1 and the mixture was treated by ultrasound at 40 KHz for 5 minutes. The mixture suspension was stirred at room temperature for 3 days to crystallize and then centrifuged. The precipitate was collected and dried under reduced pressure at 40° C. for 24 hours to give trametinib dimethyl sulfoxide solvate Form M (88.5 mg, yield 88.5%).

Example 8

Dimethyl sulfoxide (1 mL) was added to trametinib (60 mg) at 40° C. under stirring to give a pale yellow solution. The solution was cooled with a rate of 2° C. per hour to 20° C., and then the mixture was stirred at 20° C. for 16 hours. The precipitate was collected and dried under reduced pressure at 40° C. for 24 hours to give trametinib dimethyl sulfoxide solvate Form M (58.4 mg, yield 86.4%).

Its HPLC content of A impurity is 0.06 wt %.

Example 9

Dimethyl sulfoxide (3 mL) was added to trametinib (90 mg) at 50° C. with stirring to give a pale yellow solution. The solution was cooled with a rate of 10° C. per hour to 20° C., and then the mixture was stirred at 20° C. for 24 hours, Then the precipitate was collected and dried under reduced pressure at 40° C. for 20 hours to give trametinib dimethyl sulfoxide solvate Form M (75.9 mg, yield 74.8%).

Example 10

Dimethyl sulfoxide (2 mL) was added to trametinib (100 mg) at 40° C. with stirring to give a pale yellow solution. The solution was cooled with a rate of 5° C. per hour to 20° C., and the mixture was stirred at 20° C. for 10 hours. Then the precipitate was collected and dried under reduced pressure at 40° C. for 20 hours to give trametinib dimethyl sulfoxide solvate Form M (95.8 mg, yield 85.0%).

Its HPLC content of A impurity is 0.08 wt %.

The products of Examples 3 to 10 and Example 2 show the same or similar X-Ray powder diffraction pattern, TGA, DSC and IR spectrum (not shown herein), indicating products of Examples 3 to 10 are the same crystal form as trametinib dimethyl sulfoxide solvate Form M obtained in Example 2.

Example 11

Particle-Size Experimental

The particle size distribution of the rametinib dimethyl sulfoxide solvate produced by the conventional method and the trametinib dimethyl sulfoxide solvate Form M produced in Example 8 and Example 9 were determined. Results are set in FIG. 9-11 and Table 1.

TABLE 1

| Results of Particle Size Distribution | | | |
|---|---|---|---|
| Examples | $D_{10}$ (μm) | $D_{50}$ (μm) | $D_{90}$ (μm) |
| Reference Example 1 | 3 | 8 | 36 |
| Example 8 | 18 | 40 | 85 |
| Example 9 | 9 | 24 | 72 |

Figure 9:
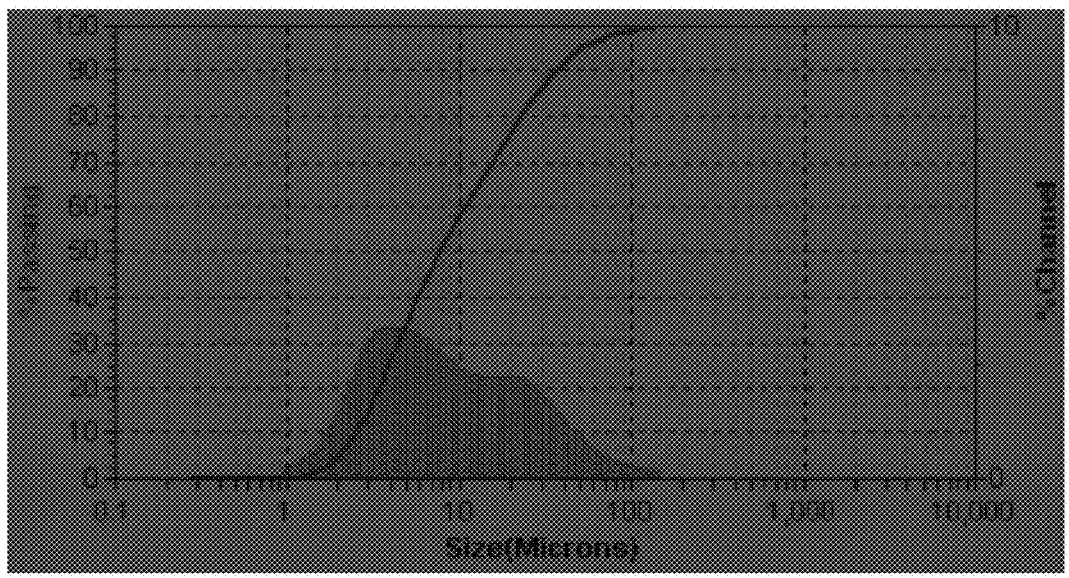
FIG. 9. Particle size distribution plot of trametinib dimethyl sulfoxide solvate prepared by conventional method described in Reference Example 1.
Figure 10:
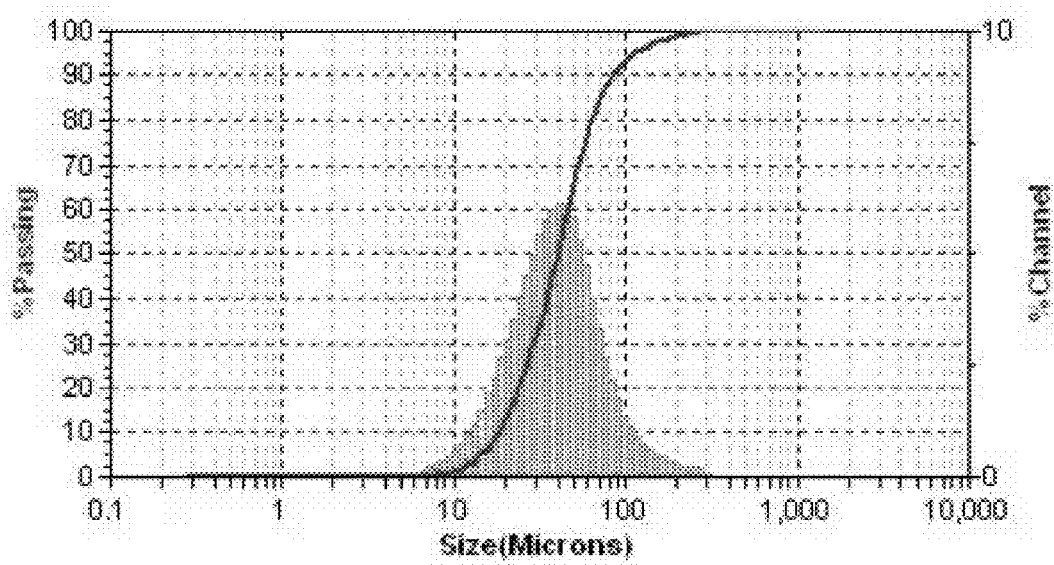
FIG. 10. Particle size distribution plot of trametinib dimethyl sulfoxide solvate Form M in Example 8.
Figure 11:
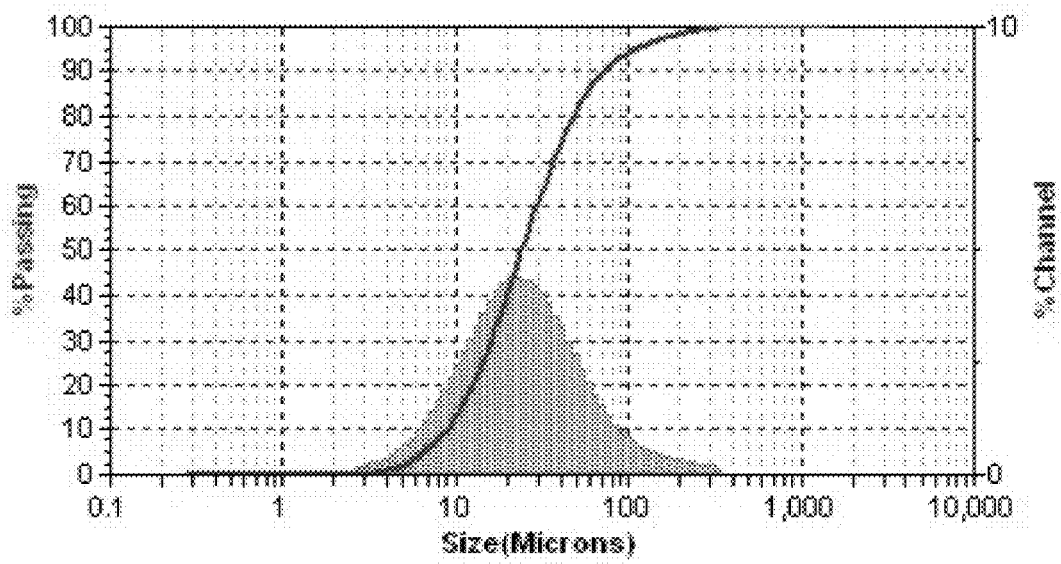
FIG. 11. Particle size distribution plot of trametinib dimethyl sulfoxide solvate Form M in Example 9.

FIG. 9 and Table 1 indicate very fine particles prepared by conventional method described in Reference Example 1; FIG. 10, FIG. 11 and Table 1 indicate larger and uniformly-distributed particles produced by the preparing method (3).

Example 12

Example of trametinib dimethyl sulfoxide solvate Form M tablets.

The ingredients are shown in Table 2.

TABLE 2

Formulation of Trametinib Dimethyl Sulfoxide Solvate Form M Tablets

| Component | Strength (mg/tablet) | | |
|---|---|---|---|
| | 0.5 | 1 | 2 |
| Trametinib dimethyl sulfoxide solvate Form M | 0.5635 | 1.127 | 2.254 |
| Sodium Lauryl Sulfate | 0.017 | 0.034 | 0.068 |
| Colloidal Silicon Dioxide | 0.01 | 0.02 | 0.04 |
| Mannitol | 95.47 | 101.509 | 106.95 |
| Microcrystalline Cellulose | 36.25 | 38.75 | 41.25 |
| Hypromellose | 7.25 | 7.75 | 8.25 |
| Croscarmellose Sodium | 4.35 | 4.65 | 4.95 |
| Magnesium Stearate | 1.09 | 1.16 | 1.24 |
| Opadry YS-1-14762-A | 0 | 0 | 4.95 |
| Opadry YS-1-12525-A | 4.35 | 0 | 0 |
| Opadry OY-S-28876 | 0 | 4.65 | 0 |
| Total Tablet Weight | 149.35 | 159.65 | 169.95 |

Preparation Steps:
1) Mix trametinib dimethyl sulfoxide solvate Form M and mannitol using geometric method in a 3D blender. Add sodium lauryl sulfate, colloidal silicon dioxide, croscarmellose sodium, microcrystalline cellulose and hypromellose and screen the mixture.
2) Magnesium stearate is screened and mixed with the mixture in step 1.
3) The mixture in step 2 was pressed into tablets using rotary tablet press. A total of 1000 tablets were made.
4) Using coating solution to continuously coat the tablets until a target weight gain of 3% was achieved. Among them, the coating material of Opadry YS-1-14762-A (pink) was used for coating 0.5 mg tablets, the coating material Opadry YS-1-12525-A (yellow) was used for coating 1 mg tablets and the coating material Opadry OY-S-28876 (white) was used for coating 2 mg tablets.

The above description of the invention is intended to be illustrative and not limiting. Various changes or modifications in the embodiments described may occur to those skilled in the art. These can be made without departing from the scope or spirit of the invention.

We claim:
1. A crystalline Form M of trametinib dimethyl sulfoxide solvate having the following formula,

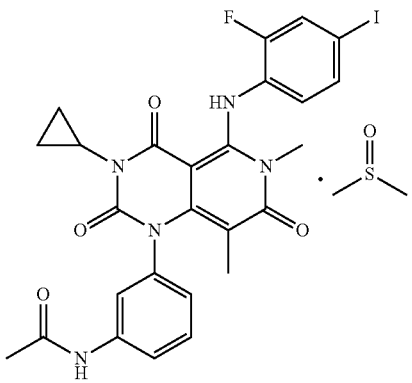

wherein the Form M is characterized by a powder X-ray diffraction pattern measured using Cu-Kα radiation comprising the following specific peaks at 2θ values: 7.8±0.2°, 11.4±0.2°, 16.8±0.2°, 18.6±0.2°, 20.0±0.2°, 23.3±0.2° and 26.5±0.2°.

2. The crystalline Form M of trametinib dimethyl sulfoxide solvate according to claim 1 wherein the Form M is characterized by a powder X-ray diffraction pattern measured using Cu-Kα radiation comprising the following specific peaks at 2θ values: 7.8±0.2°, 11.4±0.2°, 16.8±0.2°, 18.4±0.2°, 18.6±0.2°, 20.0±0.2°, 20.3±0.2°, 23.3±0.2°, 26.5±0.2° and 27.9±0.2°.

3. The crystalline Form M of trametinib dimethyl sulfoxide solvate according to claim 2, wherein the Form M is characterized by a powder X-ray diffraction pattern measured using Cu-Kα radiation comprising the following specific peaks at 2θ values: 7.8±0.2°, 11.4±0.2°, 16.8±0.2°, 18.4±0.2°, 18.6±0.2°, 20.0±0.2°, 20.3±0.2°, 20.9±0.2°, 21.1±0.2°, 23.3±0.2°, 25.4±0.2°, 26.5±0.2°, 27.9±0.2° and 28.3±0.2°.

4. The crystalline Form M of trametinib dimethyl sulfoxide solvate according to claim 1, wherein the Fourier transform infrared spectrum of the Form M comprises the following characteristic peaks expressed by wavenumbers at 791, 1034, 1280, 1304, 1319, 1418, 1489, 1544, 1589, 1635 and 3079 cm$^{-1}$.

5. The crystalline Form M of trametinib dimethyl sulfoxide solvate according to claim 1, wherein $D_{50}$ is at least 10 μm, and/or $D_{10}$ is at least 5 μm, and/or $D_{90}$ is at least 30 μm.

6. A pharmaceutical composition comprising an effective amount of the crystalline Form M of trametinib dimethyl sulfoxide solvate according to claim 1 and at least one pharmaceutically acceptable excipient.

7. The pharmaceutical composition according to claim 6, wherein the Form M is characterized by a powder X-ray diffraction pattern measured using Cu-Kα radiation comprising the following specific peaks at 2θ values: 7.8±0.2°, 11.4±0.2°, 16.8±0.2°, 18.4±0.2°, 18.6±0.2°, 20.0±0.2°, 20.3±0.2°, 23.3±0.2°, 26.5±0.2° and 27.9±0.2°.

8. The pharmaceutical composition according to claim 7, wherein the Form M is characterized by a powder X-ray diffraction pattern measured using Cu-Kα radiation comprising the following specific peaks at 2θ values: 7.8±0.2°, 11.4±0.2°, 16.8±0.2°, 18.4±0.2°, 18.6±0.2°, 20.0±0.2°, 20.3±0.2°, 20.9±0.2°, 21.1±0.2°, 23.3±0.2°, 25.4±0.2°, 26.5±0.2°, 27.9±0.2° and 28.3±0.2°.

9. The pharmaceutical composition according to claim 6, wherein the Fourier transform infrared spectrum of the Form M comprises the following characteristic peaks expressed by wavenumbers at 791, 1034, 1280, 1304, 1319, 1418, 1489, 1544, 1589, 1635 and 3079 cm$^{-1}$.

10. A pharmaceutical composition comprising an effective amount of the crystalline Form M of trametinib dimethyl sulfoxide solvate according to claim 1 and at least one pharmaceutically acceptable excipient, wherein the Form M is prepared according to a process selected from one of the following methods (1), (2), or (3):

(1) suspending trametinib in dimethyl sulfoxide, stirring at room temperature for 3-10 days to crystallize and recovering the crystalline Form M of trametinib dimethyl sulfoxide solvate;

(2) suspending another trametinib dimethyl sulfoxide solvate Form other than Form M in dimethyl sulfoxide, stirring at room temperature for 3-10 days to crystallize and recovering the crystalline Form M of trametinib dimethyl sulfoxide solvate; and (3) cooling the solution of trametinib in dimethyl sulfoxide from 50° C. to 20° C. at a rate of 2-10° C./hour, stirring at 20° C. for 10-24 hours and recovering the crystalline Form M of trametinib dimethyl sulfoxide solvate.

11. A method for inhibiting mitogen-activated protein kinase activity in a patient having a hyperproliferative disorder, comprising administering to a patient in need thereof an effective amount of the crystalline Form M of trametinib dimethyl sulfoxide solvate according to claim 1 or the pharmaceutical composition according to claim 6, wherein the hyperproliferative disorder is selected from the group consisting of brain tumor, esophageal cancer, gastric cancer, liver cancer, pancreatic cancer, colorectal cancer, lung cancer, kidney cancer, breast cancer, ovarian cancer, prostate cancer, skin cancer, melanoma, neuroblastoma and sarcoma.

12. The method according to claim 11, wherein the Form M is characterized by a powder X-ray diffraction pattern measured using Cu-Kα radiation comprising the following specific peaks at 2θ values: 7.8±0.2°, 11.4±0.2°, 16.8±0.2°, 18.4±0.2°, 18.6±0.2°, 20.0±0.2°, 20.3±0.2°, 23.3±0.2°, 26.5±0.2° and 27.9±0.2°.

13. The method according to claim 12, wherein the Form M is characterized by a powder X-ray diffraction pattern measured using Cu-Kα radiation comprising the following specific peaks at 2θ values: 7.8±0.2°, 11.4±0.2°, 16.8±0.2°, 18.4±0.2°, 18.6±0.2°, 20.0±0.2°, 20.3±0.2°, 20.9±0.2°, 21.1±0.2°, 23.3±0.2°, 25.4±0.2°, 26.5±0.2°, 27.9±0.2° and 28.3±0.2°.

14. The method according to claim 11, wherein the Fourier transform infrared spectrum of the Form M comprises the following characteristic peaks expressed by wavenumbers at 791, 1034, 1280, 1304, 1319, 1418, 1489, 1544, 1589, 1635 and 3079 cm$^{-1}$.

15. A process for preparing the crystalline Form M of trametinib dimethyl sulfoxide solvate according to claim 1, which is selected from one of the following methods (1), (2), or (3):

(1) suspending trametinib in dimethyl sulfoxide, stirring at room temperature for 3-10 days to crystallize and recovering the crystalline Form M of trametinib dimethyl sulfoxide solvate;

(2) suspending another trametinib dimethyl sulfoxide solvate Form other than Form M in dimethyl sulfoxide, stirring at room temperature for 3-10 days to crystallize and recovering the crystalline Form M of trametinib dimethyl sulfoxide solvate; and (3) cooling the solution of trametinib in dimethyl sulfoxide from 50° C. to 20° C. at a rate of 2-10° C./hour, stirring at 20° C. for 10-24 hours and recovering the crystalline Form M of trametinib dimethyl sulfoxide solvate.

16. The process according to claim 15, wherein:

in method (1), the ratio of trametinib and dimethyl sulfoxide is 30-50 mg:1 mL, and the duration of crystallization is 3-7 days; and in method (2), the ratio of another trametinib dimethyl sulfoxide solvate Form other than Form M and dimethyl sulfoxide is 30-50 mg: 1 mL, and the duration of crystallization is 3-7 days; and in method (3), the concentration of the solution of trametinib in dimethyl sulfoxide is 30-60 mg/mL;

the solution is cooled from 40° C. to 20° C.;

the cooling rate is 2-5° C./hour; and the duration of stirring is 10-16 hours.

17. The process according to claim 16, wherein:

in method of (1), the ratio of trametinib and dimethyl sulfoxide is 40-50 mg:1 mL;

in method (2), the ratio of another trametinib dimethyl sulfoxide solvate Form other than Form M and dimethyl sulfoxide is 40-50 mg:1 mL; and in method (3), the concentration of the solution of trametinib in dimethyl sulfoxide is 50-60 mg/mL.

18. A process for preparing a pharmaceutical composition comprising admixing an effective amount of a crystalline Form M of trametinib dimethyl sulfoxide solvate with at least one pharmaceutically acceptable excipient, wherein the crystalline Form M of trametinib dimethyl sulfoxide solvate has the following formula,

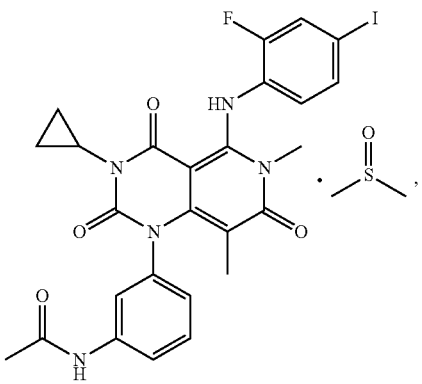

and wherein the Form M is characterized by a powder X-ray diffraction pattern measured using Cu-Kα radiation comprising the following specific peaks at 2θ values: 7.8±0.2°, 11.4±0.2°, 16.8±0.2°, 18.6±0.2°, 20.0±0.2°, 23.3±0.2° and 26.5±0.2°.

19. The process according to claim 18, wherein the Form M is characterized by a powder X-ray diffraction pattern measured using Cu-Kα radiation comprising the following specific peaks at 2θ values: 7.8±0.2°, 11.4±0.2°, 16.8±0.2°, 18.4±0.2°, 18.6±0.2°, 20.0±0.2°, 20.3±0.2°, 23.3±0.2°, 26.5±0.2° and 27.9±0.2°.

20. The process according to claim 19, wherein the Form M is characterized by a powder X-ray diffraction pattern measured using Cu-Kα radiation comprising the following specific peaks at 2θ values: 7.8±0.2°, 11.4±0.2°, 16.8±0.2°, 18.4±0.2°, 18.6±0.2°, 20.0±0.2°, 20.3±0.2°, 20.9±0.2°, 21.1±0.2°, 23.3±0.2°, 25.4±0.2°, 26.5±0.2°, 27.9±0.2° and 28.3±0.2°.

21. The process according to claim 18, wherein the Fourier transform infrared spectrum of the Form M comprises the following characteristic peaks expressed by wavenumbers at 791, 1034, 1280, 1304, 1319, 1418, 1489, 1544, 1589, 1635 and 3079 cm$^{-1}$.

22. A crystalline Form M of trametinib dimethyl sulfoxide solvate having the following formula,

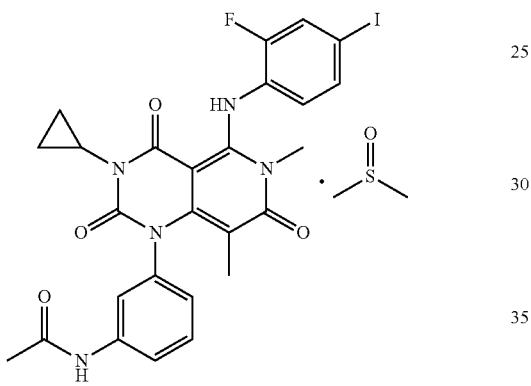

wherein the Form M is characterized by a powder X-ray diffraction pattern measured using Cu-Kα radiation comprising the following specific peaks at 2θ values: 7.8±0.2°, 11.4±0.2°, 16.8±0.2°, 18.6±0.2°, 20.0±0.2°, 23.3±0.2° and 26.5±0.2°, wherein the Form M contains less than 0.15% by weight of A impurity,

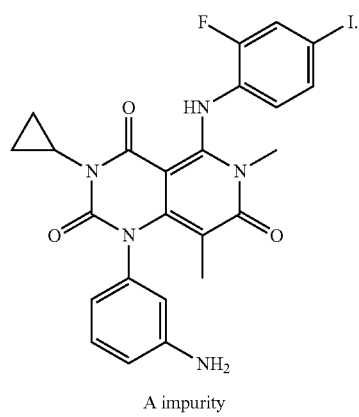 [SMILES: Cc1c(=O)n(C)c(Nc2ccc(I)cc2F)c2c(=O)n(C3CC3)c(=O)n(-c3cccc(N)c3)c12]

A impurity

23. A crystalline Form M of trametinib dimethyl sulfoxide solvate having the following formula,

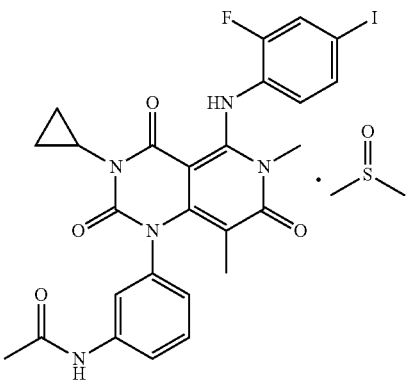

wherein the Form M is characterized by a powder X-ray diffraction pattern measured using Cu-Kα radiation comprising the following specific peaks at 2θ values: 7.8±0.2°, 11.4±0.2°, 16.8±0.2°, 18.6±0.2°, 20.0±0.2°, 23.3±0.2° and 26.5±0.2°, wherein when stored at 44% relative humidity under room temperature for 9 months, its X-ray diffraction pattern shows no signs of form change.

* * * * *